United States Patent
Wang

(10) Patent No.: US 9,625,433 B2
(45) Date of Patent: Apr. 18, 2017

(54) INTAKE ANALYSIS SYSTEM AND METHOD

(71) Applicants: INVENTEC APPLIANCES (PUDONG) CORPORATION, Shanghai (CN); INVENTEC APPLIANCES CORP., New Taipei (TW); INVENTEC APPLIANCES (NANCHANG) CORPORATION, Nanchang (CN); INVENTEC APPLIANCES (SHANGHAI) CO., LTD., Shanghai (CN)

(72) Inventor: Chang-Tao Wang, Nanchang (CN)

(73) Assignees: Inventec Appliances (Pudong) Corporation, Shanghai (CN); Inventec Appliances Corp., New Taipei (TW); Inventec Appliances (Nanchang) Corporation, Nanchang (CN); Inventec Appliances (Shanghai) Co., Ltd., Shanghai (CN)

( * ) Notice: Subject to any disclaimer, the term of this patent is extended or adjusted under 35 U.S.C. 154(b) by 938 days.

(21) Appl. No.: 13/949,954

(22) Filed: Jul. 24, 2013

(65) Prior Publication Data

US 2014/0032121 A1    Jan. 30, 2014

(30) Foreign Application Priority Data

Jul. 26, 2012  (CN) .......................... 2012 1 0260328

(51) Int. Cl.
 *G01N 33/48* (2006.01)
 *G01N 33/02* (2006.01)
 *G06F 19/00* (2011.01)

(52) U.S. Cl.
 CPC .......... *G01N 33/02* (2013.01); *G06F 19/3481* (2013.01); *G06F 19/3475* (2013.01)

(58) Field of Classification Search
 CPC .................................................... G06F 19/3481
 USPC ........................................................ 702/19
 See application file for complete search history.

Primary Examiner — Jerry Lin
(74) Attorney, Agent, or Firm — Muncy, Geissler, Olds & Lowe, P.C.

(57) ABSTRACT

Disclosed are an intake analysis system and a method thereof comprising an intake sensing device and a cloud computing device. The intake sensing device may be installed in a container containing an ingesta, providing for analyzing a component of the ingesta to generate a detecting signal, and sensing a weight variation of the container having the ingesta therein to generate a weight sensing signal; the cloud computing device receives the detecting signal and weight sensing signal transmitted and calculates a calorie value and an intake value to generate substance ingested information, and compares the calorie value and the intake value. When the calorie value or intake value is greater than a predetermined value respectively, the cloud computing device generates a noticing signal, and transmits the substance ingested information and noticing signal to the intake sensing device, and the intake sensing device displays the substance ingested information and noticing information.

10 Claims, 3 Drawing Sheets

INTAKE ANALYSIS SYSTEM AND METHOD

This application claims the benefit of China Patent No. 201210260328.8, filed on Jul. 26, 2012, in the State Intellectual Property Office of the People's Republic of China, the disclosure of which is incorporated herein in its entirety by reference.

FIELD OF THE INVENTION

The present invention relates to an intake analysis system and an intake analysis method, and more particularly to the intake analysis system and method being capable of computing values such as the intake, calorie and temperature of ingesta of an animal or a plant by cloud computing and feeding back the information to notice users.

BACKGROUND OF THE INVENTION

For maintaining good health or pursuing a perfect figure, most people control their calories through exercises and diet. At present, some manufacturers combine a music player with sneakers to provide a sport kit for users, and a sensor is installed into a built-in groove of an insole of the users' sport shoes, and a receiver is installed at the users' music player. The sensor is provided for tracing the pace of a user's exercise, and then transmitting the information to the receiver of the music player. When the user is running or jogging, the music player can display the time, distance and speed of the user's jogging and the calories consumed. Therefore, the user can know the calorie consumption during the exercise, so as to achieve the aforementioned objective.

However, the aforementioned way of controlling health through this exercise method has the drawbacks as following:

1. Since the calories are consumed by exercise after the calories have been intaken, therefore this way cannot control the calorie intake directly, and users who do not like sports, a good effect cannot be achieved.
2. The aforementioned method can control the user's calorie consumption, but this method is inapplicable for animals and plants.
3. At present, the aforementioned method does not provide a cloud service, and thus failing to achieve a timed reminding function.

SUMMARY OF THE INVENTION

In view of the aforementioned problems of the prior art, it is a primary objective of the present invention to provide an intake analysis system and an intake analysis method to overcome the problems of the conventional way of examining the calorie consumption through a sport device that fails to provide an effect health control.

To achieve the aforementioned objective, the present invention provides an intake sensing device and a cloud computing device. The intake sensing device is movably disposed at a container having ingesta therein and configured for analyzing a component of the ingesta to generate a detecting signal, and sensing a weight variation of the container having the ingesta therein to generate a weight sensing signal. The cloud computing device is configured for receiving the detecting signal and the weight sensing signal transmitted from the intake sensing device, and computing a calorie value and an intake value to generate substance ingested information, and the cloud computing device further compares the calorie value with the intake value, wherein if the calorie value or the intake value is greater than a predetermined value, the cloud computing device generates a noticing signal, and the cloud computing device transmits the substance ingested information and the noticing signal to the intake sensing device, so as to display the substance ingested information and noticing information on the intake sensing device.

Preferably, the intake sensing device is further configured for sensing a temperature of the ingesta to generate a temperature sensing signal, and the cloud computing device is further configured for generating a temperature value based on the temperature sensing signal, and the temperature value is included in the substance ingested information.

Preferably, the intake sensing device includes a calorie detecting module, a weight sensing module, a temperature sensing module, a transmitting module and a display module. The calorie detecting module is configured for detecting the component of the ingesta, the weight sensing module is configured for sensing the weight variation of the container having the ingesta therein, the temperature sensing module is configured for sensing the temperature of the ingesta, and the transmitting module is configured for transmitting the detecting signal. The weight sensing signal and the temperature sensing signal are transmitted to the cloud computing device and used for receiving the substance ingested information, and the display module is configured for displaying the substance ingested information.

Preferably, the calorie detecting module is a near infrared ray measuring meter that emits a near infrared ray to the ingesta to obtain an absorption rate of the ingesta and generate the detecting signal, and the cloud computing device receives the detecting signal to compute the calorie value with respect to the ingesta in accordance with the absorption rate.

Preferably, the cloud computing device further stores the substance ingested information.

Preferably, the cloud computing device further compares the temperature value with the predetermined value. If the temperature value is greater than the predetermined value, the cloud computing device generates the noticing signal and transmits the noticing signal to the intake sensing device, and the noticing information is displayed by the intake sensing device.

Preferably, the noticing information includes words, images, light signal or voice.

To achieve the aforementioned objective, the present invention further provides an intake analysis method, comprising the steps of: analyzing a component of an ingesta in a container so as to generate a detecting signal; sensing a weight variation of the container having the ingesta therein to generate a weight sensing signal; utilizing a cloud computing device to receive the detecting signal and the weight sensing signal transmitted and compute a calorie value and an intake value to generate a substance ingested information; comparing the calorie value with the intake value, wherein if the calorie value or the intake value is greater than a predetermined value respectively, the cloud computing device generating a noticing signal; and displaying the substance ingested information and noticing information.

In summation, the intake analysis system and method of the present invention have one or more of the following advantages:

(1) The intake analysis system and method provide users a way of obtaining information including the intake, calorie value and temperature of the food intaken through the detection of calorie, intake and temperature and the cloud computing during a food intake process and allowing users to use the information as a basis for their health control, so as to achieve the weight reduction effectively.

(2) The intake analysis system and method are not only applicable for people, but also applicable for animals and plants if an intake sensing device is installed in an intake container (a pet vessel or a plant watering device) to achieve the same intake control effect.

(3) The intake analysis system and method adopt cloud computing, and the intake information and noticing information is transmitted to an intake sensing device by cloud, so as to achieve the effect of noticing the users.

DESCRIPTION OF THE PREFERRED EMBODIMENTS

The technical characteristics, contents, advantages and effects of the present invention will become apparent from the following detailed description taken with the accompanying drawing. All figures are drawn for ease of explanation of the basic teachings of the present invention only; the extensions of the figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Figure 1:
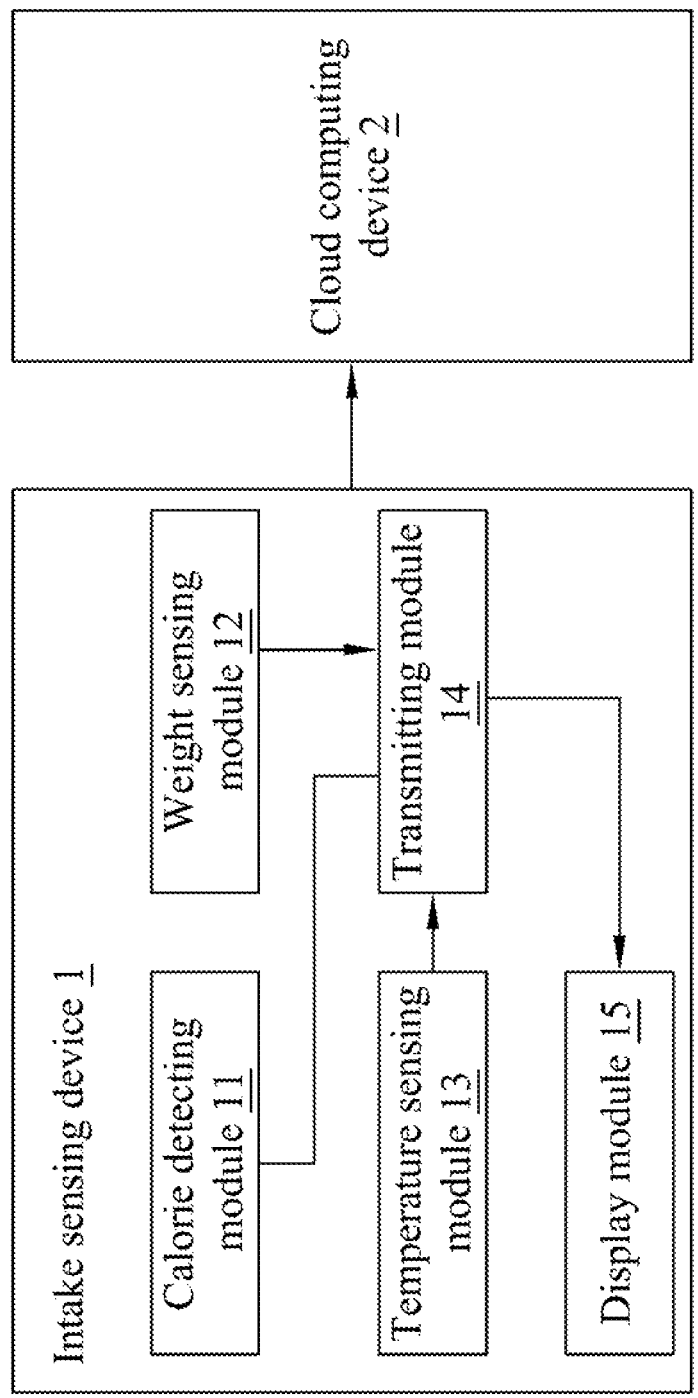
FIG. 1 is a block diagram of an intake analysis system of the present invention.

With reference to FIG. 1 for a block diagram of an intake analysis system of the present invention, the intake analysis system comprises an intake sensing device 1 and a cloud computing device 2. The intake sensing device 1 is installed in a container, wherein the container can be a general bowl, cup or tray, or a pet vessel, or a plant watering device for containing ingesta. The intake sensing device 1 includes a calorie detecting module 11, a weight sensing module 12, a temperature sensing module 13, a transmitting module 14 and a display module 15. The calorie detecting module 11, the weight sensing module 12, the temperature sensing module 13 and the display module 15 are coupled to the transmitting module 14. The calorie detecting module 11 can be a calorie near infrared ray measuring meter for measuring the calorie of a substance. The weight sensing module 12 is a weight sensor, and the temperature sensing module 13 is a temperature sensor. The transmitting module 14 is provided for transmitting information via network. The display module 15 includes an LCD or LED display.

Wherein, the intake sensing device 1 detects and analyzes a component of the ingesta in the container through the calorie detecting module 11 to generate a detecting signal, and senses a weight variation of the container containing the ingesta through the weight sensing module 12 to generate a weight sensing signal. The transmitting module 14 is provided for transmitting the detecting signal and the weight sensing signal to the cloud computing device 2, such that the cloud computing device 2 can calculate a calorie value and an intake value according to the detecting signal and the weight sensing signal to generate a substance ingested information. After the cloud computing device 2 transmits the substance ingested information to the intake sensing device 1, the intake sensing device 1 displays the substance ingested information from the display module 15. Therefore, users can examine their food intake and calories from the displayed substance ingested information to achieve the health control effect. In addition, the temperature sensing module 13 is provided for detecting the temperature of the ingesta to generate a temperature sensing signal, and the cloud computing device 2 generates a temperature value according to the temperature sensing signal, wherein the temperature value is included in the substance ingested information. Therefore, the users can further know about the temperature of their food intake. Since the calorie detecting module 11 can be a calorie near infrared ray measuring meter, therefore the near infrared ray can be projected onto the ingesta to obtain an absorption rate of the ingesta to generate a detecting signal, and the cloud computing device 2 is provided for receiving the detecting signal to calculate the corresponding calorie value of the ingesta according to the absorption rate.

Wherein, after the cloud computing device 2 generates the substance ingested information, the information is stored. In addition, the cloud computing device 2 further executes a comparison function to compare the calorie value, the intake value and the temperature value. If the calorie value, the intake value or the temperature value is greater than a predetermined value respectively, the cloud computing device 2 will generate and transmit a noticing signal to the intake sensing device 1, and the intake sensing device 1 will display noticing information to remind the users. If the users have too much food, an excessive quantity of calories or a too-high temperature, the cloud computing device 2 will issue a warning to the intake sensing device 1. Wherein, the noticing information may be displayed in form of words, images, light signals or voices.

Figure 2:
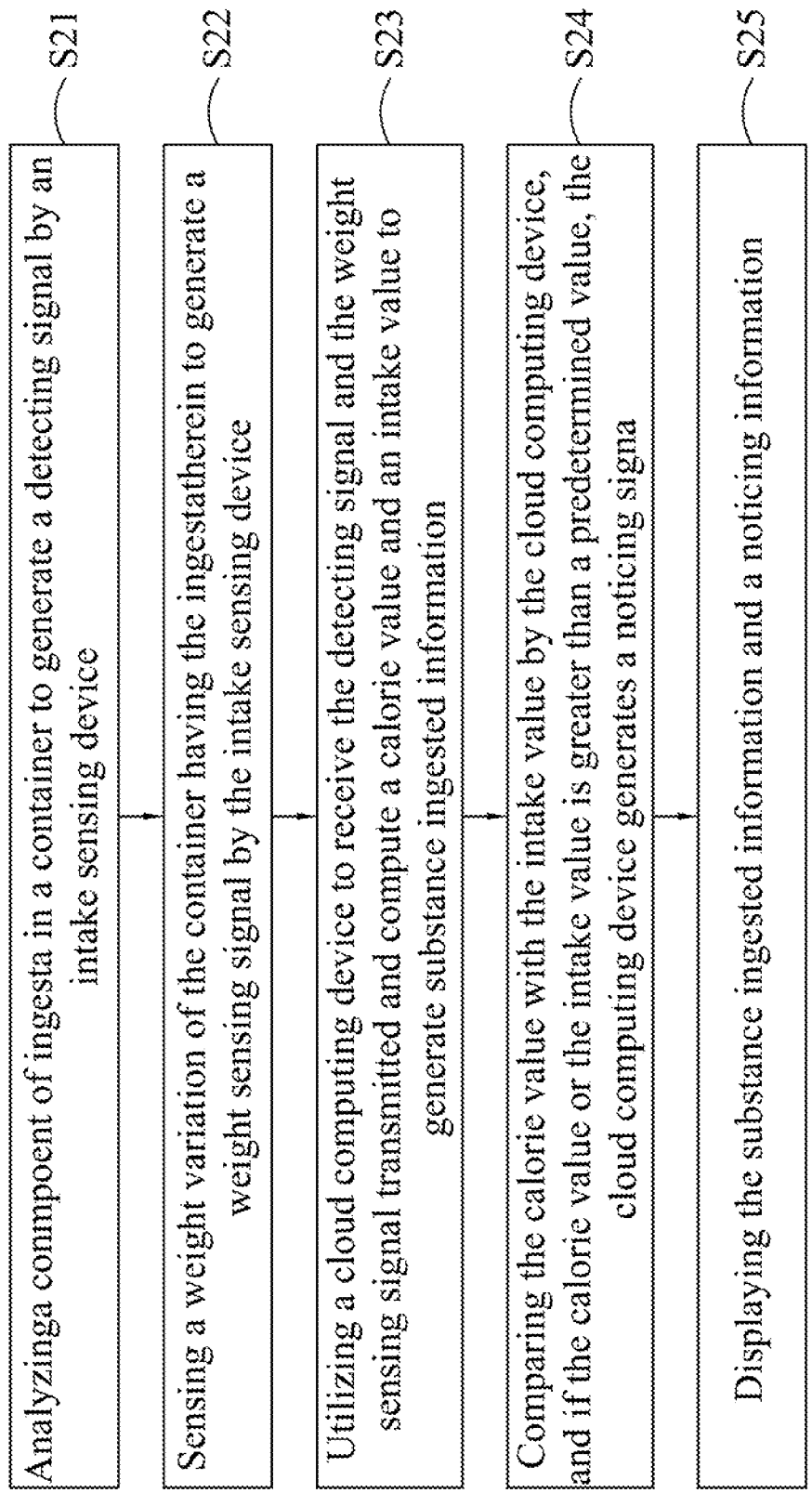
FIG. 2 is a flow chart of an intake analysis method of the present invention.

With reference to FIG. 2 for a flow chart of an intake analysis method of the present invention, the intake analysis method comprises the following steps:

S21: Analyzing a component of ingesta in a container to generate a detecting signal by an intake sensing device.

S22: Sensing a weight variation of the container having the ingesta therein to generate a weight sensing signal by the intake sensing device.

S23: Utilizing a cloud computing device to receive the detecting signal and the weight sensing signal transmitted and compute a calorie value and an intake value to generate substance ingested information.

S24: Comparing the calorie value with the intake value by the cloud computing device, and if the calorie value or the intake value is greater than a predetermined value, the cloud computing device generates a noticing signal.

S25: Displaying the substance ingested information and a noticing information.

Figure 3:
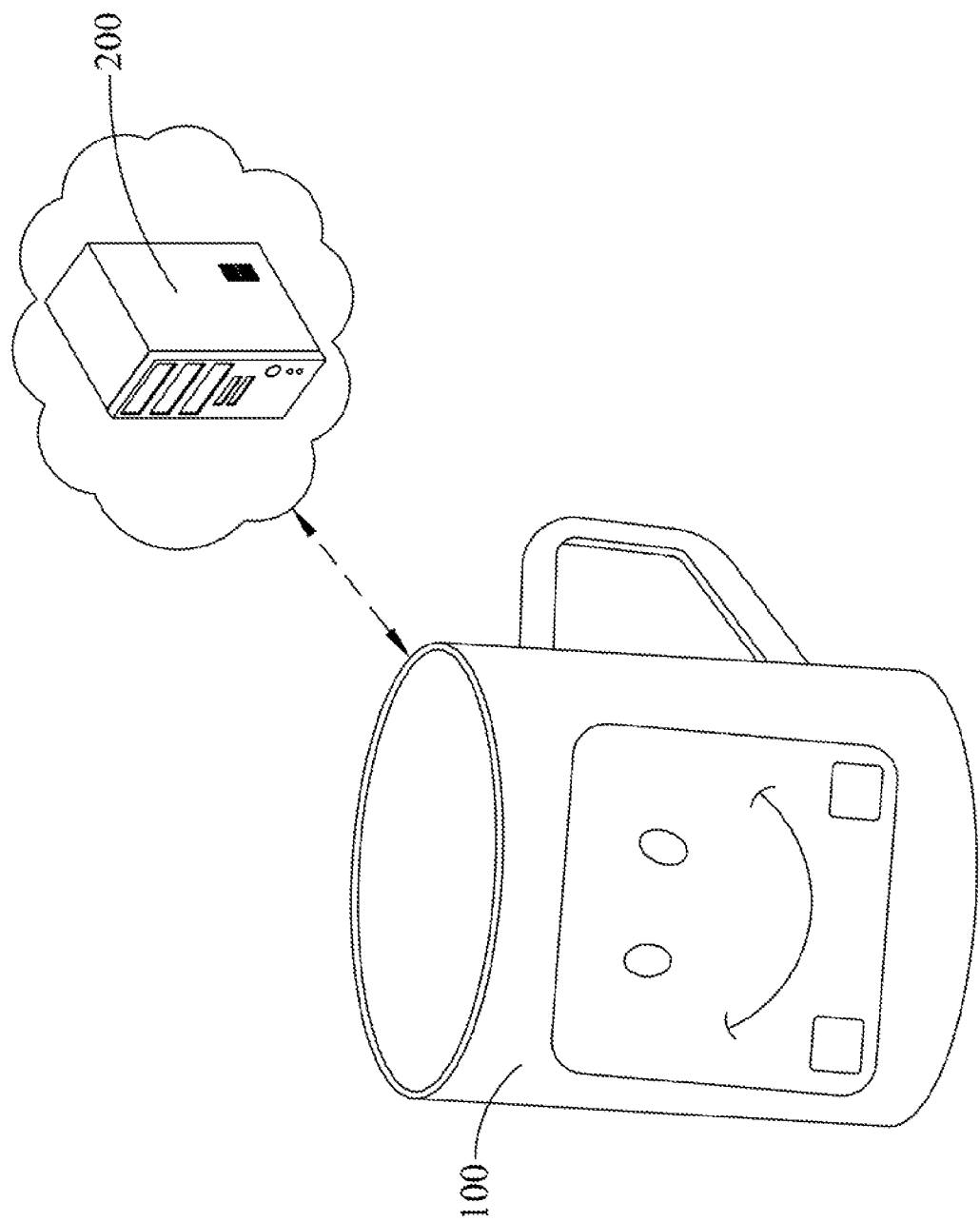
FIG. 3 is a schematic view of an intake analysis system and an intake analysis method of a preferred embodiment of the present invention.

With reference to FIG. 3 for a schematic view of an intake analysis system and an intake analysis method of a preferred embodiment of the present invention, the intake analysis system comprises a general cup container 100 having ingesta such as water, drink or soup therein. The cup container 100 further includes the intake sensing device of the present invention installed therein, and the intake sensing device is provided for detecting the calorie of the ingesta in the cup container 100 and sensing the temperature of the ingesta. If a user drinks the ingesta, the intake sensing device will sense a weight variation of the cup container 100. If the intake sensing device senses each of the aforementioned information, the information will be transmitted to the cloud computing device 200 via network, and the cloud computing device 200 will calculate each of the information. Therefore, the calorie value of the ingesta intaken by the user, the temperature value of the ingesta and the intake value can be calculated, and the calculated values will be transmitted back to the intake sensing device and displayed from the intake sensing device. Therefore, the user can know about the total calories intake and the temperature according to the aforementioned information to control the food intake and avoid the issue of having excessive intake or obesity. The cloud computing device 200 compares the information, and if the value of the information exceeds a standard value, then a noticing signal will be issued and sent to the intake sensing device to notice the user. For example, if the ingesta are filled into the original cup container 100 to a specific quantity, the intake sensing device will display a smile-face icon, and if the user drinks the ingesta and the ingesta becomes less gradually, the smile-face icon is changed to a crying-face icon. Wherein, the way for the intake sensing device to display the noticing information is not limited to the aforementioned icons only, but it can be in form of words, sounds or lights.

In summation of the description above, the intake analysis system and method of the present invention can have the intake sensing device installed in a user's drinking container, a pet vessel or a plant watering device, such that the intake sensing device can detect the information including the calorie, the intake and the temperature of the ingesta filled into the aforementioned containers, and the cloud computing device is provided for calculation to produce actual data. After the cloud computing device calculates the data, and transmits the noticing signal to the intake sensing device, the intake of the users, their pets or plants and the temperature and the calorie value can be noticed, so as to achieve the intake control effect.

While the invention has been described by means of specific embodiments, numerous modifications and variations could be made thereto by those skilled in the art without departing from the scope and spirit of the invention set forth in the claims.

What is claimed is:

1. An intake analysis system, comprising:
   an intake sensing device, movably disposed at a container having an ingesta therein, the intake sensing device being configured for analyzing a component of the ingesta to generate a detecting signal, and sensing a weight variation of the container having the ingesta therein to generate a weight sensing signal;
   a cloud computing device, being configured for receiving the detecting signal and the weight sensing signal transmitted from the intake sensing device, and computing a calorie value and an intake value to generate a substance ingested information, the cloud computing device further comparing the calorie value with the intake value, wherein if the calorie value or the intake value is greater than a predetermined value respectively, the cloud computing device generating a noticing signal, and the cloud computing device transmitting the substance ingested information and the noticing signal to the intake sensing device, so as to display the substance ingested information and a noticing information on the intake sensing device.

2. The intake analysis system of claim 1, wherein the intake sensing device is further configured for sensing a temperature of the ingesta to generate a temperature sensing signal, and the cloud computing device is further configured for generating a temperature value based on the temperature sensing signal, and the temperature value is included into the substance ingested information.

3. The intake analysis system of claim 2, wherein the intake sensing device includes a calorie detecting module, a weight sensing module, a temperature sensing module, a transmitting module and a display module, the calorie detecting module being configured for detecting the component of the ingesta, the weight sensing module being configured for sensing the weight variation of the container having the ingesta therein, the temperature sensing module being configured for sensing the temperature of the ingesta, the transmitting module being configured for transmitting the detecting signal, the weight sensing signal and the temperature sensing signal being transmitted to the cloud computing device and used for receiving the substance ingested information, and the display module being configured for displaying the substance ingested information.

4. The intake analysis system of claim 3, wherein the calorie detecting module is a near infrared ray measuring meter that emits a near infrared ray to the ingesta to obtain an absorption rate of the ingesta and generates the detecting signal, and the cloud computing device receives the detecting signal to compute the calorie value with respect to the ingesta in accordance with the absorption rate.

5. The intake analysis system of claim 2, wherein the cloud computing device further stores the substance ingested information.

6. The intake analysis system of claim 2, wherein the cloud computing device further compares the temperature value with the predetermined value, if the temperature value is greater than the predetermined value, the cloud computing device generating the noticing signal and transmitting the noticing signal to the intake sensing device, and the noticing information being displayed by the intake sensing device.

7. The intake analysis system of claim 6, wherein the noticing information includes words, images, light signal or voice.

8. An intake analysis method, comprising the following steps of:
   analyzing a component of an ingesta in a container so as to generate a detecting signal by using an intake sensing device, movably disposed at the container;
   sensing a weight variation of the container having the ingesta therein to generate a weight sensing signal by using the intake sensing device;
   utilizing a cloud computing device to receive the detecting signal and the weight sensing signal transmitted and compute a calorie value and an intake value to generate a substance ingested information;
   comparing the calorie value with the intake value by using the cloud computing device, wherein if the calorie value or the intake value is greater than a predetermined value respectively, the cloud computing device generating a noticing signal; and
   displaying the substance ingested information and a noticing information by using the intake sensing device.

9. The intake analysis method of claim 8 further comprising:
   detecting a temperature of the ingesta to generate a temperature sensing signal by using the intake sensing device; and
   generating a temperature value based on the temperature sensing signal by using the intake sensing device, and including the temperature value into the substance ingested information through the cloud computing device.

10. The intake analysis method of claim 9, further comprising:
utilizing the cloud computing device to compare the temperature value with the predetermined value, wherein if the temperature value is greater than the predetermined value thereof, generating the noticing signal and displaying the noticing signal.

\* \* \* \* \*